(12) United States Patent
Kenyon et al.

(10) Patent No.: US 6,216,691 B1
(45) Date of Patent: Apr. 17, 2001

(54) MOUNTING BODY (75) Inventors: Barton John Kenyon, Dumdleton (GB); Alexander Virr, Balmain (AU); Marek Tomasz Sapula, Parramatta (AU); Philip Rodney Kwok, West Pymble (AU); Peter John Deacon Wickham, Five Dock (AU)

(73) Assignee: ResMed Limited, North Ryde (AU)

( * ) Notice: Subject to any disclaimer, the term of this patent is extended or adjusted under 35 U.S.C. 154(b) by 0 days.

(21) Appl. No.: 09/185,875

(22) Filed: Nov. 3, 1998

(30) Foreign Application Priority Data

Nov. 3, 1997 (AU) .................................................. PP0150

(51) Int. Cl.$^7$ .................................................. A61M 11/00
(52) U.S. Cl. ................................ 128/205.18; 128/204.18
(58) Field of Search ........................ 128/205.18, 204.18, 128/200.24; 248/638, 634; 181/212

(56) References Cited

U.S. PATENT DOCUMENTS

| 3,099,985 | 8/1963 | Wilson et al. . |
|---|---|---|
| 3,502,100 | 3/1970 | Jonson . |
| 3,726,270 | 4/1973 | Griffis et al. . |
| 3,741,208 | 6/1973 | Jonsson et al. . |
| 3,914,994 | 10/1975 | Banner . |

(List continued on next page.)

FOREIGN PATENT DOCUMENTS

| 4-70516 | 3/1992 | (JP) . |
|---|---|---|
| WO 93/08857 | 5/1993 | (WO) . |
| WO 93/09834 | 5/1993 | (WO) . |
| WO 93/21982 | 11/1993 | (WO) . |

Primary Examiner—Aaron J. Lewis
Assistant Examiner—Teena Mitchell
(74) Attorney, Agent, or Firm—Pillsbury Madison & Sutro LLP (57) ABSTRACT

A mounting body (10) for mounting a flow generator assembly (13) within an external housing. The body (10) is formed from a compliant material and is adapted to be fixed with respect to the housing. The body (10) also includes a recess of substantially complementary shape to the flow generator assembly (13) to receive and locate same.

Also disclosed is an apparatus for providing breathable gas to a patient. The apparatus includes an external apparatus housing, the flow generator assembly (13) and the mounting body (10).

29 Claims, 8 Drawing Sheets

U.S. PATENT DOCUMENTS

| | | |
|---|---|---|
| 3,995,661 | 12/1976 | Van Fossen . |
| 4,119,096 | 10/1978 | Drews . |
| 4,206,754 | 6/1980 | Cox et al. . |
| 4,312,235 | 1/1982 | Daigle . |
| 4,396,034 | 8/1983 | Cherniak . |
| 4,449,525 | 5/1984 | White et al. . |
| 4,481,944 | 11/1984 | Bunnell . |
| 4,519,399 | 5/1985 | Hori . |
| 4,558,710 | 12/1985 | Eichler . |
| 4,579,114 | 4/1986 | Gray et al. . |
| 4,592,880 | 6/1986 | Murakami . |
| 4,677,975 | 7/1987 | Edgar et al. . |
| 4,747,403 | 5/1988 | Gluck et al. . |
| 4,773,411 | 9/1988 | Downs . |
| 4,802,485 | 2/1989 | Bowers et al. . |
| 4,819,629 | 4/1989 | Jonson . |
| 4,856,506 | 8/1989 | Jinotti . |
| 4,905,789 | 3/1990 | Francis ................................ 181/224 |
| 4,928,684 | 5/1990 | Breitenfelder et al. . |
| 4,938,210 | 7/1990 | Shene . |
| 4,957,107 | 9/1990 | Sipin . |
| 4,986,269 | 1/1991 | Hakkinen . |
| 4,989,599 | 2/1991 | Carter . |
| 5,046,491 | 9/1991 | Derrick . |
| 5,048,515 | 9/1991 | Sanso . |
| 5,063,922 | 11/1991 | Hakkinen . |
| 5,063,938 | 11/1991 | Beck et al. . |
| 5,099,837 | 3/1992 | Russel, Sr. et al. . |
| 5,107,830 | 4/1992 | Younes . |
| 5,107,831 | 4/1992 | Halpern et al. . |
| 5,129,390 | 7/1992 | Chopin et al. . |
| 5,148,802 | 9/1992 | Sanders et al. . |
| 5,165,398 | 11/1992 | Bird . |
| 5,178,138 | 1/1993 | Walstrom et al. . |
| 5,199,424 | 4/1993 | Sullivan et al. ................ 128/204.18 |
| 5,203,343 | 4/1993 | Axe et al. . |
| 5,230,330 | 7/1993 | Price . |
| 5,231,979 | 8/1993 | Rose et al. ...................... 128/204.14 |
| 5,231,983 | 8/1993 | Matson et al. . |
| 5,239,994 | 8/1993 | Atkins . |
| 5,239,995 | 8/1993 | Estes et al. . |
| 5,245,995 | 9/1993 | Sullivan et al. . |
| 5,280,784 | 1/1994 | Kohler . |
| 5,303,698 | 4/1994 | Tobia et al. . |
| 5,303,700 | 4/1994 | Weismann et al. . |
| 5,311,875 | 5/1994 | Stasz . |
| 5,322,057 | 6/1994 | Raabe et al. . |
| 5,335,656 | 8/1994 | Bowe et al. . |
| 5,339,850 | 8/1994 | Mertz ..................................... 135/72 |
| 5,373,842 | 12/1994 | Olsson et al. . |
| 5,388,571 | 2/1995 | Roberts et al. . |
| 5,394,870 | 3/1995 | Johansson ...................... 128/205.22 |
| 5,398,673 | 3/1995 | Lambert . |
| 5,400,777 | 3/1995 | Olsson et al. . |
| 5,404,871 | 4/1995 | Goodman et al. . |
| 5,443,061 | 8/1995 | Champain et al. . |
| 5,458,137 | 10/1995 | Axe et al. . |
| 5,479,920 | 1/1996 | Piper et al. . |
| 5,501,433 | 3/1996 | Satori ............................. 267/140.13 |
| 5,509,404 | 4/1996 | Lloyd et al. . |
| 5,509,414 | 4/1996 | Hok . |
| 5,535,739 | 7/1996 | Rapoport et al. . |
| 5,546,933 | 8/1996 | Rapoport et al. . |
| 5,590,648 | 1/1997 | Mitchell . |
| 5,608,647 | 3/1997 | Rubsamen et al. . |
| 5,633,552 | 5/1997 | Lee et al. . |
| 5,642,730 | 7/1997 | Baran . |
| 5,655,520 | 8/1997 | Howe et al. . |
| 5,655,522 | 8/1997 | Mechlenburg et al. ......... 128/203.12 |
| 5,673,687 | 10/1997 | Dobson et al. ................. 128/204.14 |
| 5,713,082 | 2/1998 | Bassette et al. .......................... 2/412 |
| 5,715,812 | 2/1998 | Deighan et al. ................ 128/204.23 |

MOUNTING BODY

FIELD OF THE INVENTION

The present invention relates to a mounting body for mounting a flow generator assembly within an external housing and an apparatus for providing breathable gas to a patient.

The invention has been developed primarily for use in breathable gas supply apparatus used in, for example, the Continuous Positive Airway Pressure (CPAP) treatment of Obstructive Sleep Apnea (OSA) and similar sleep disordered breathing conditions. The invention also finds application in breathable gas delivery systems used for assisted ventilation and mechanical respiration.

BACKGROUND OF THE INVENTION

The pressurised gas supplied in CPAP treatment of OSA serves to pneumatically splint open the patient's airways. The pressure of the supplied gas may be constant, bi-level (in synchronism with patient breathing) or auto-setting in level. Throughout this specification any reference to CPAP is intended to incorporate a reference to any one of, or combinations of, these forms of breathable gas supply.

CPAP treatment is generally administered whilst the patient and any bed partner are sleeping. As the gas supply apparatus is normally located within a few meters of the patient it is desirable to minimise the noise produced by that apparatus to minimise sleep disturbance.

CPAP breathable gas supply apparatus generally comprise a plastics housing or casing having a gas flow generator assembly and an electrical control and power supply system therein. A flexible conduit connects the outlet of the apparatus (at a point on the housing) to a nose and/or mouth mask worn by the patient to communicate the supplied gas to the patient's airways.

The flow generator assembly usually consists of a brushless electric motor driving a fan or turbine. The noise produced by the flow generator assembly has three basic transmission paths to surrounding atmosphere. It is radiated from the apparatus housing, transmitted from the turbine outlet to be propagated along the conduit that connects the outlet of the apparatus to the patient mask and transmitted from the turbine inlet to be propagated along the gas inlet path (in the opposite direction to the gas flow) to the housing gas inlet and so to atmosphere.

In a prior art approach, the flow generator assembly has been mounted to the apparatus housing by fastening the turbine housing to mounting feet integrally moulded with the apparatus casing with cushioning rubber washers disposed between the housing and feet. In addition to having acoustic air paths for noise emanating from the flow generator through the conduit and housing, vibration produced by the flow generator assembly is transmitted through the feet to the housing, which acts as a panel radiator, and radiates noise therefrom. The vibration energy reaching the casing can also result in a buzzing noise or the like that can be particularly disturbing to the patient and any bed partner.

An attempt to reduce noise radiated from the housing has involved attaching numerous, for example about ten, blocks of acoustically absorptive foam to the inner surfaces of the apparatus housing. However, this increases the complexity, and thereby the cost, of assembling the apparatus.

Another approach is used in the applicant's bi-level CPAP apparatus model VPAPII. The VPAPII includes a sound enclosure within the apparatus housing having an outlet chamber mounted therein. The metal sound enclosure has a first and second chamber, each having a port to allow the passage of air into the first chamber through to, and then out of, the second chamber. The flow generator assembly and the outlet chamber are located in the second chamber. Air is drawn past a baffle and into the first chamber which includes a step-like labyrinth baffle allowing the free flow of air through the first chamber into the second chamber whilst attenuating the noise from the flow generator assembly propagating along the air inlet path. The internal surfaces of the sound enclosure are lined with sound absorbing polyurethane skinned foam.

In one version of VPAPII, the flow generator assembly is mounted within the sound enclosure and attached to the outlet chamber by a rigid metal mounting bracket. In another earlier version, the flow generator assembly sat on one inner face of the second chamber and was cushioned by EVA foam that was in turn adhered to the second chamber inner face. In both versions, the blower air path outlet is secured to the inlet port of the outlet chamber by way of a silicone rubber conduit.

The outlet chamber is formed as one substantially rectangular chamber moulded from "ignition resistant" ABS. Foam is adhered to the outlet chamber's internal surfaces but otherwise the outlet chamber is 'empty' in that it has no labyrinthine or tortuous path.

The VPAPII, whilst being quieter than previous apparatus, requires expensive materials to produce, is complex in both manufacture and assembly and does not allow for rapid reassembly after servicing. It also utilises steel components which are relatively heavy and affect the portability of the apparatus.

It is an object of the present invention to substantially overcome or at least ameliorate one or more of the deficiencies of the prior art.

SUMMARY OF THE INVENTION

Accordingly, in a first aspect, the present invention discloses a mounting body for mounting a flow generator assembly within an external housing, the body being formed from a compliant material and adapted to be fixed with respect to said housing and including a recess of substantially complementary shape to said flow generator assembly to receive and locate same.

In a second aspect, the present invention discloses an apparatus for providing breathable gas to a patient, the apparatus includes an external apparatus housing, a flow generator assembly, and a mounting body of compliant material fixed with respect to said housing including a recess of complementary shape to said flow generator assembly to receive and locate same.

In the present specification, the terminology "compliant material" is intended to encompass any material having the ability to absorb vibrations, for example in the manner of an acoustic dampening foam, as well as being sufficiently structurally rigid to achieve a mounting function and support the weight of the flow generator assembly.

Examples of compliant material are:

(1) Polyurethane, being a foamed thermo-setting plastic. The foam can be, for example, polyester-polyurethane foam or polyether-polyurethane foam; and (2) An elastomer such as foamed silicone.

Preferably, the mounting body includes one or more external surfaces adapted to be complementary to, and engage with, adjacent internal surfaces of the housing to locate the body with respect to the housing.

The mounting body is preferably produced from a single piece of compliant material. Alternatively, the body may be formed from a plurality of compliant components fitted, adhered or otherwise bonded to one another.

The flow generator assembly is preferably snugly received, and desirably substantially enveloped, within the recess of the body. Any exposed surfaces of the flow generator assembly are preferably covered by a filter foam insert of complementary shape to the recess.

The body is preferably adapted to mount the flow generator in isolation from any contact with the housing.

The flow generator recess in the body preferably includes an orifice for allowing gas to communicate with the inlet of the flow generator, In an embodiment, the mounting body preferably includes at least one wall disposed, after assembly, adjacent an internal wall of said housing, said body wall including channel means which co-operate with said housing internal wall to provide an inlet duct from atmosphere to said orifice. If desired, a layer of compliant material can be disposed between the housing wall and the body, the layer co-operating with the channel means to form the inlet duct In another embodiment, the inlet duct is formed internal of the mounting body.

The inlet duct is preferably a tortuous path to reduce noise propagating from the flow generator assembly to the apparatus air inlet.

The flow generator recess is desirably on the opposite side of the mounting body to the inlet duct with the orifice providing fluid communication therebetween.

In a further embodiment, the mounting body includes a plurality of depressions, perforations, honeycombs, sub-ducts or sub-channels opening from the channel means and/or inlet duct and extending away therefrom into said mounting body.

In a yet her embodiment, the mounting body is releasably mounted to the apparatus housing of the breathable gas providing apparatus so as to permit removal and replacement of the mounting body to achieve replacement, cleaning and/or sterilization of the channels means and/or the inlet duct that constitutes the gas flow path through the mounting body.

The mounting body can also, in preferred forms, be shaped for supporting and locating other components of the breathable gas providing apparatus. As an example, the mounting body can include a recess to receive and locate an electrical control panel. Alternatively, the mounting body can include one or more protuberances or other support structures to support said control panel

BRIEF DESCRIPTION OF THE DRAWINGS

Embodiments of the present invention will now be described, by way of examples only, with reference to the accompanying drawings in which.

DESCRIPTION OF THE PREFERRED EMBODIMENTS

Figure 1:
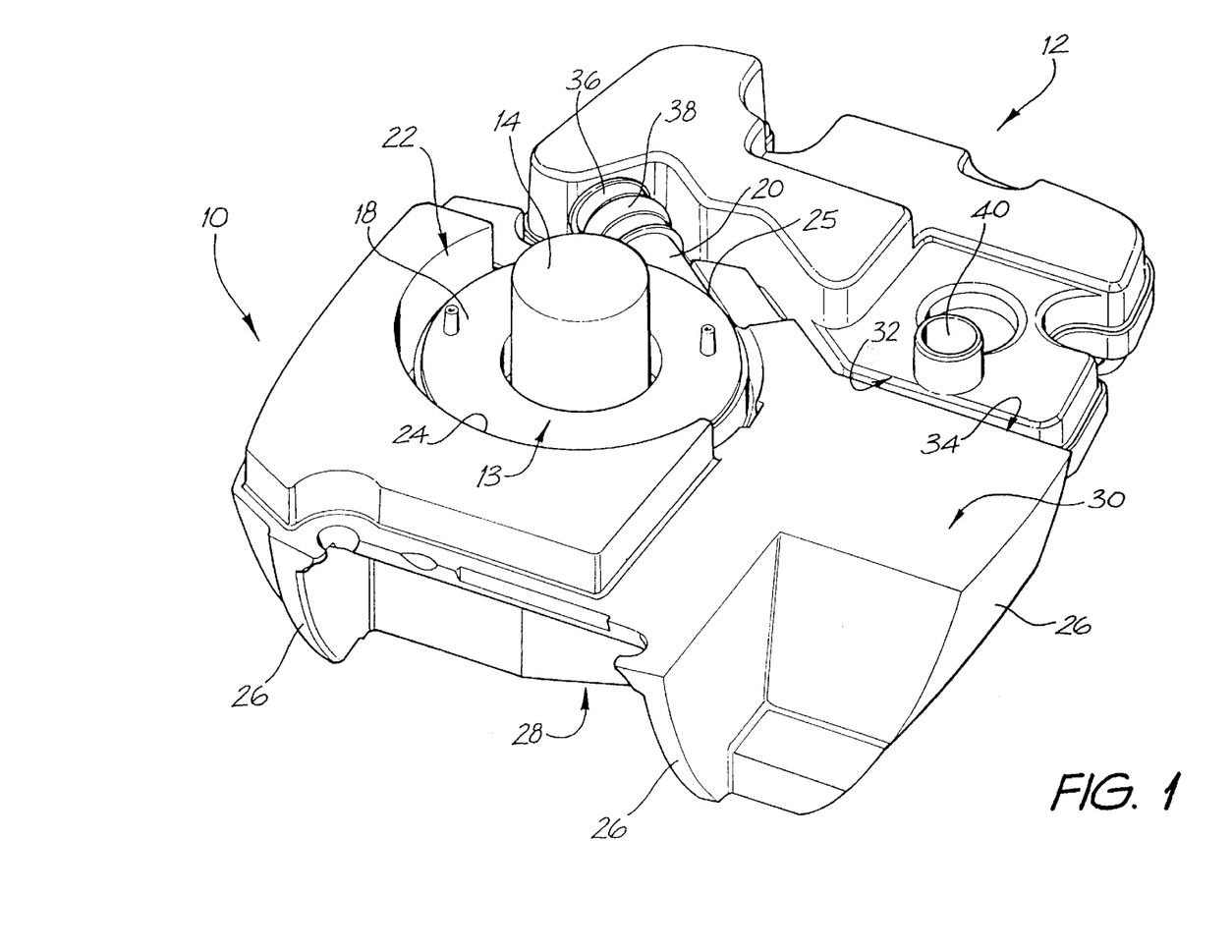
FIG. 1 is a perspective view of the first embodiment of the mounting body shown adjacent a complementary shaped muffler.
Figure 2:
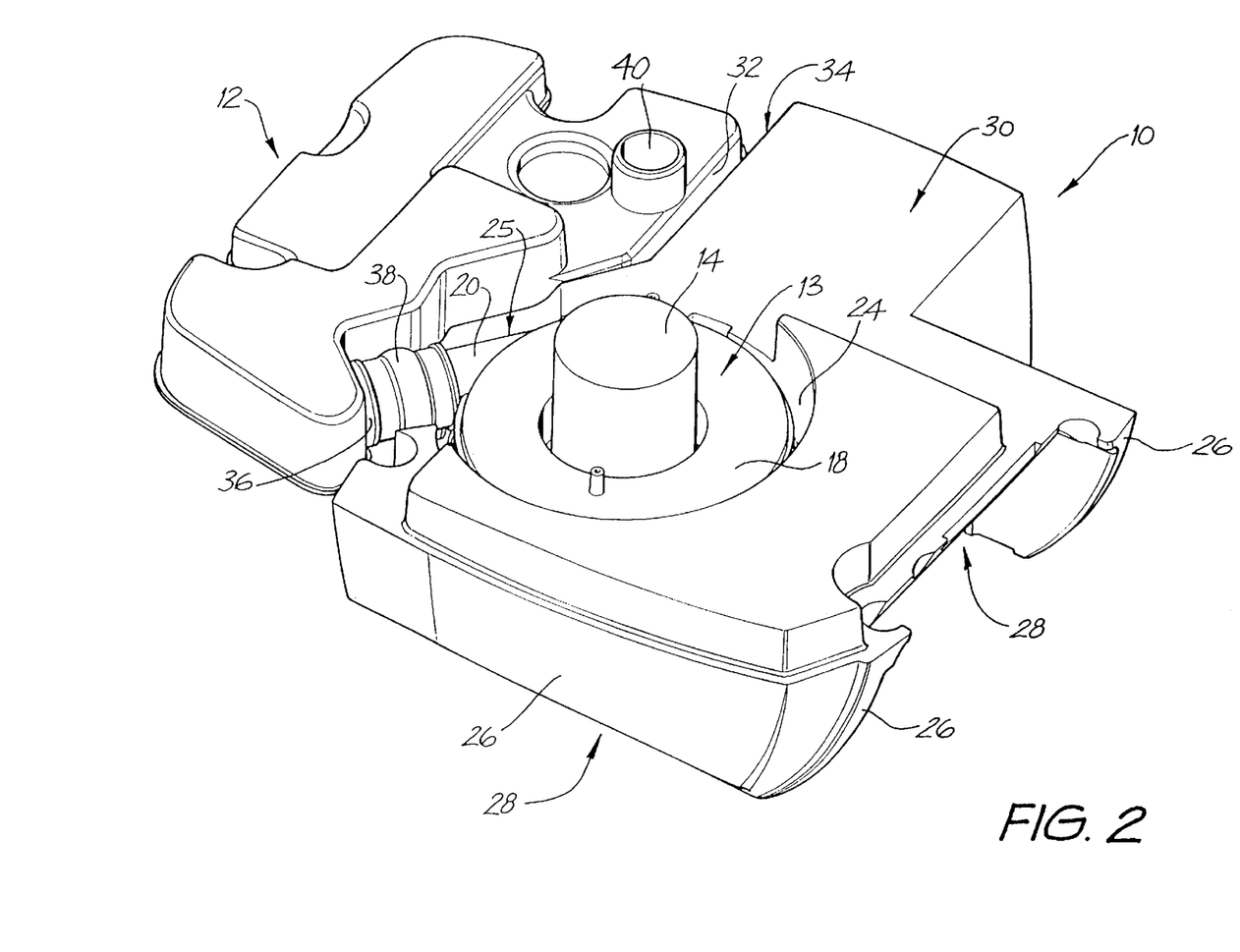
FIG. 2 is a perspective view of the body shown in FIG. 1 rotated by approximately 90°.
Figure 3:
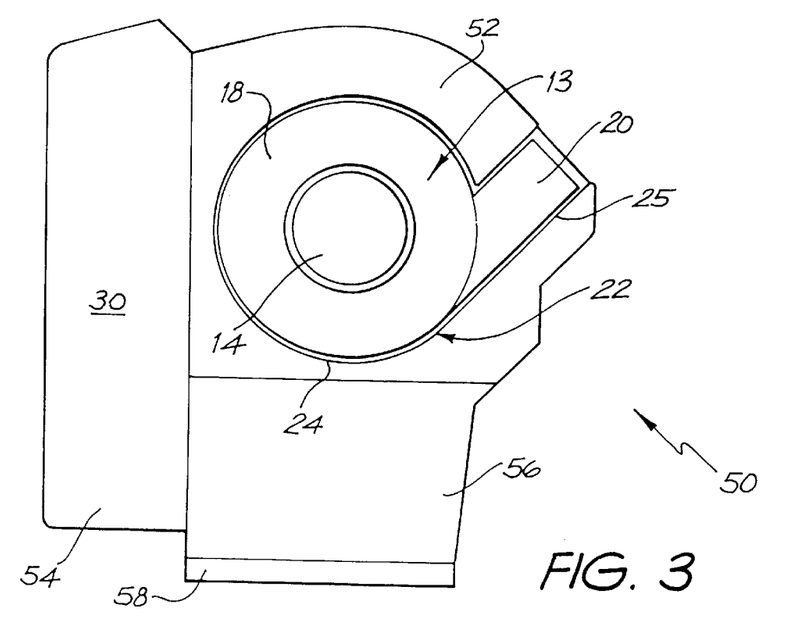
FIG. 3 is a plan view of a second embodiment of a mounting body.

FIGS. 1 and 2 show a first embodiment of a mounting body 10 according to the invention adjacent a complementary shaped muffler 12 for use within the housing of a breathable gas supply apparatus (not shown). A flow generator assembly 13 is located within the mounting body 10 as will be hereinafter explained in more detail. The flow generator assembly 13 comprises a brushless electric motor 14 which drives a turbine (not shown) within a toroidal turbine housing 18 and a tangential outlet duct 20.

The mounting body 10 is formed from a substantially open cell polyurethane foam having acoustic absorptive properties, such as 1SF-1350 type manufactured by URE-TEC.

It will be appreciated that although this foam is described as open cell, the terms open cell and closed cell are applicable to two extreme positions. Between the two extremes there is a continuum of variations. The flow resistivity of a foam is used to determine its degree of openness. The preferred acoustic absorptive quality will be found in a foam that is located on the closed side of the middle of the range from open to closed but not at the closed cell extreme. This will ensure that the foam is sufficiently open to absorb noise, sufficiently structurally rigid to provide the necessary mechanical support for the flow generator assembly and also sufficiently resilient to provide vibrational dampening.

Returning to FIGS. 1 and 2, the body 10 includes a recess 22 comprising a cylindrical depression 24 of substantially complementary shape to the turbine housing 18 and a channel 25 of substantially complementary shape to the outlet duct 20. The recess 22 is thus sized and shaped to be a snug fit around the exterior of the flow generator assembly 13. The flow generator assembly 13 and the body 10 are assembled into a common unit by pressing the flow generator assembly 13 down into the recess 22.

The outermost surfaces of the sides 26 and underside 28 of the body 10 are shaped to be substantially complementary to adjacent internal walls and bottom of the apparatus housing (not shown). The flow generator/body unit is assembled into the housing by placing the unit within the housing and securing it relative to the housing by a cover plate (not shown) which extends across top surface 30 of the body 10 and lightly squeezes or sandwiches the body 10 between the plate and the bottom of the housing.

In FIGS. 1 and 2, the muffler 12 is provided with a side wall 32 which is of a complementary shape to adjacent side wall 34 of the body 10. Inlet 36 of the muffler 12 is thereby advantageously positioned substantially adjacent the flow generator outlet duct 20 for connecting thereto by a straight coupling 38. The muffler 12 also has an outlet 40. The outer sides and underside of the muffler 12 are similarly of a complementary shape to adjacent sides and bottom of the apparatus housing.

The underside 28 of the body 10 includes channels (not shown) to provide gas communication from atmosphere to the apparatus housing gas inlet and so to a turbine inlet (not shown) located underneath and central of the toroidal turbine housing 18. The channels are shown in, and will be more specifically explained with reference to, the second and third embodiments of the mounting body described below.

FIGS. 3 to 6 show a second embodiment of a mounting body 50 in accordance with the present invention in which like features to those previously described in relation to the first embodiment are denoted by like reference numerals. The mounting body 50 is formed from four foam pieces 52, 54, 56 and 58 which are adhered to one another. It will be appreciated, however, that the body can be produced from a single piece of foam or numerous pieces fitted, adhered or otherwise bonded to one another.

Figure 4:
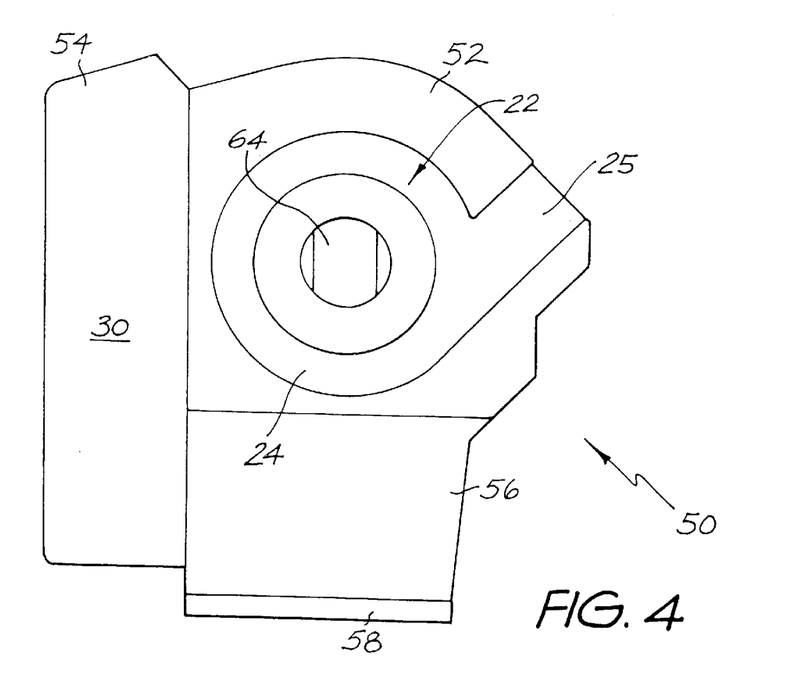
FIG. 4 is a plan view of the body shown in FIG. 3 with the flow generator removed.

The recess 22 in the body 50 is best seen in FIG. 4. As with the first embodiment, the recess 22 is comprised of cylindrical depression 24, to receive the turbine housing 18, and the channel 25, to receive the outlet duct 20.

Figure 5:
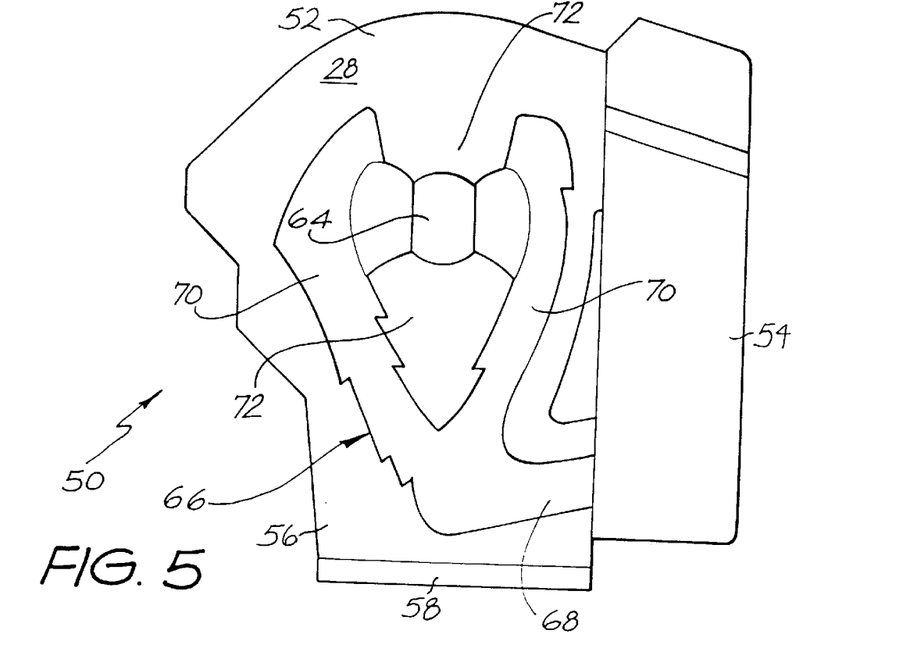
FIG. 5 is an underside plan view of the body shown in FIG. 4.

As best shown in FIGS. 4 and 5, the body 50 includes an orifice 64 in the centre of the cylindrical depression 24. After assembly, the orifice 64 is adjacent the inlet (not shown) of the turbine housing 18. As shown in FIG. 5, the underside 28 of the body 50 includes a recess indicated generally at 66 to communicate the gas surrounding the apparatus housing to the orifice 64 and so to the turbine housing inlet. The recess 66 comprises an inlet channel 68 joining two further channels 70 which communicate gas to the orifice 64. The two channels 70 are positioned either side of underside body portions 72 which serve to support the centre of the body 50 beneath the flow generator 13 and stop the body 50 flexing under the weight of the flow generator assembly 13 and restricting the channels 68 and 70.

When assembled, the underside 28 of the body 50 is disposed substantially flush and adjacent to the bottom of the apparatus housing which, in co-operation with the channels 68 and 70, forms inlet ducts of substantially rectangular cross-section.

Alternatively, the body 50 can be formed with internal channels or a layer of compliant material can be disposed between the underside 28 at the body 50 and the bottom of the housing so that all surfaces of the inlet duct are compliant material.

Further, the opening of the inlet duct 68 can also be moulded to the shape of the gas inlet in the apparatus housing. This effectively seals the inlet ducts to the housing gas inlet and ensures air is only drawn through the inlet and not other openings which can create noise. Moreover, this also ensures that all inlet air will be drawn through any filters or the like.

Figure 6:
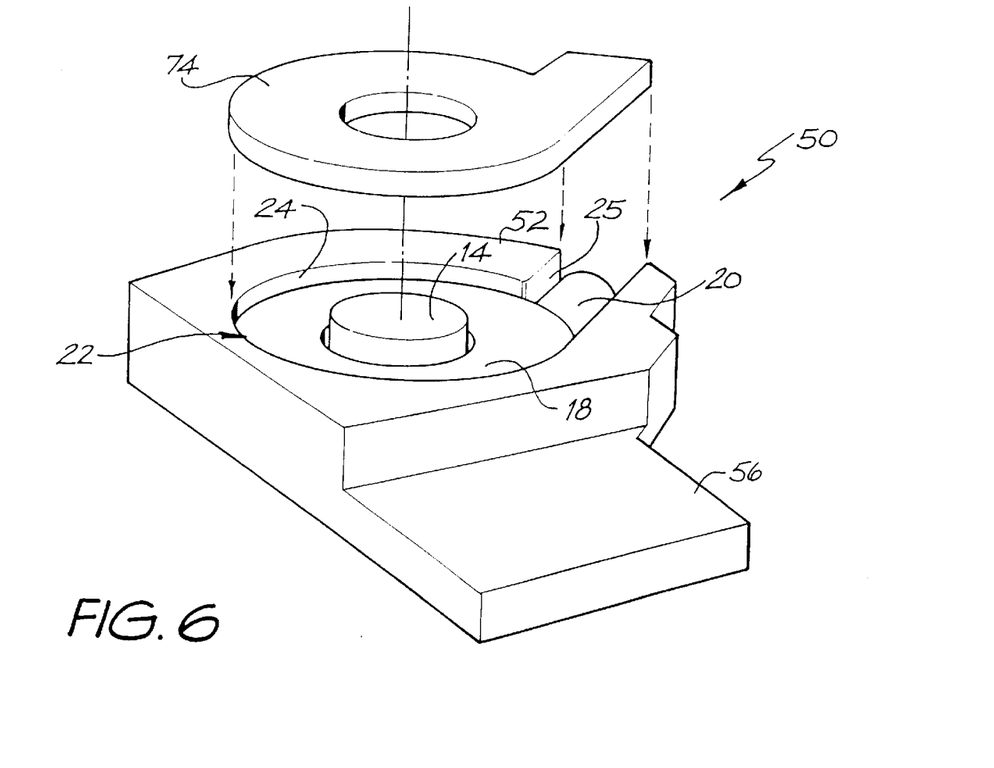
FIG. 6 is a plan view to FIG. 4 including a further resilient body in exploded relation.

As previously stated, the body 50 is located within the breathable gas supply apparatus housing with its top and bottom surface 30 and 28 sandwiched between the bottom of the flow generator housing and cover plate. FIG. 6 shows a foam mounting insert 74 which is of complementary shape to the flow generator 13 and which is placed between the flow generator 13 and the mounting plate to cover the exposed surface of the flow generator assembly 13 and snugly sandwich the flow generator assembly 13 within the boundaries of the body 50 and in isolation from direct contact from the cover plate and apparatus housing.

Figure 7:
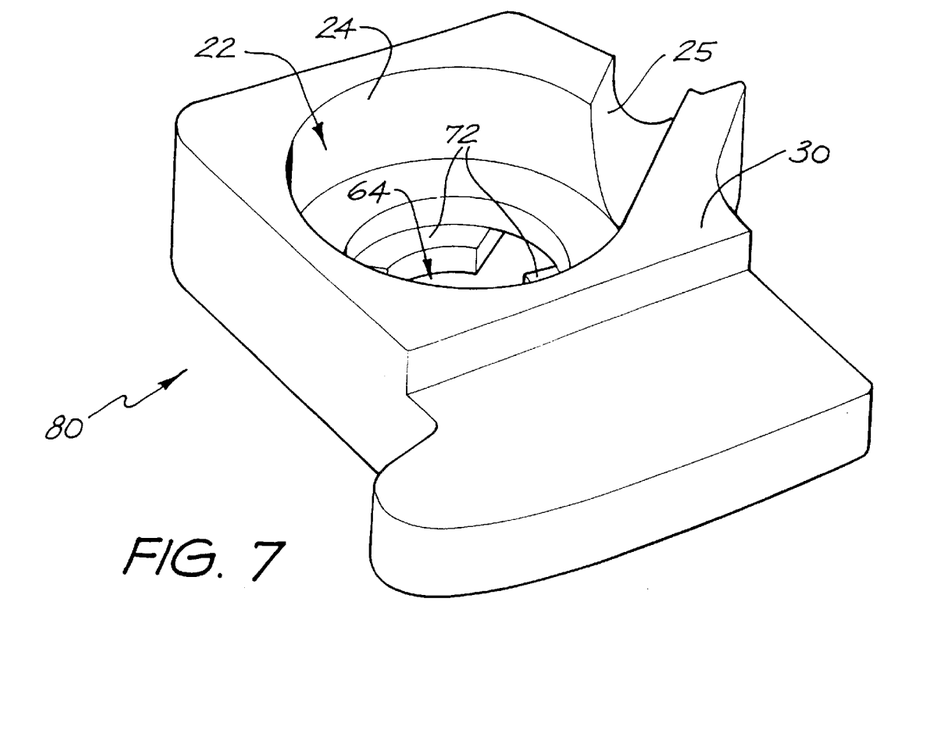
FIG. 7 is a perspective view of a third embodiment of a mounting body.
Figure 8:
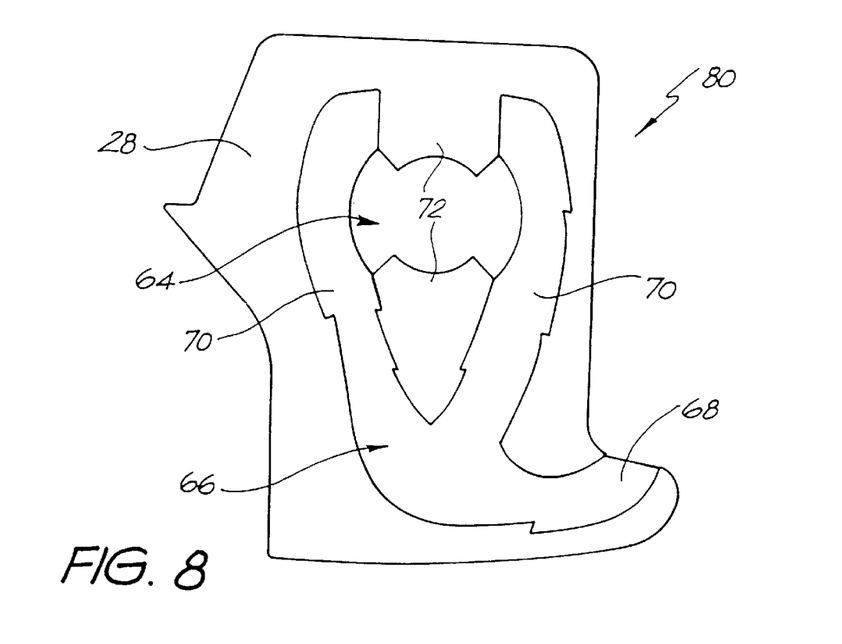
FIG. 8 is an underside plan view of the body shown in FIG. 7.
Figure 9:
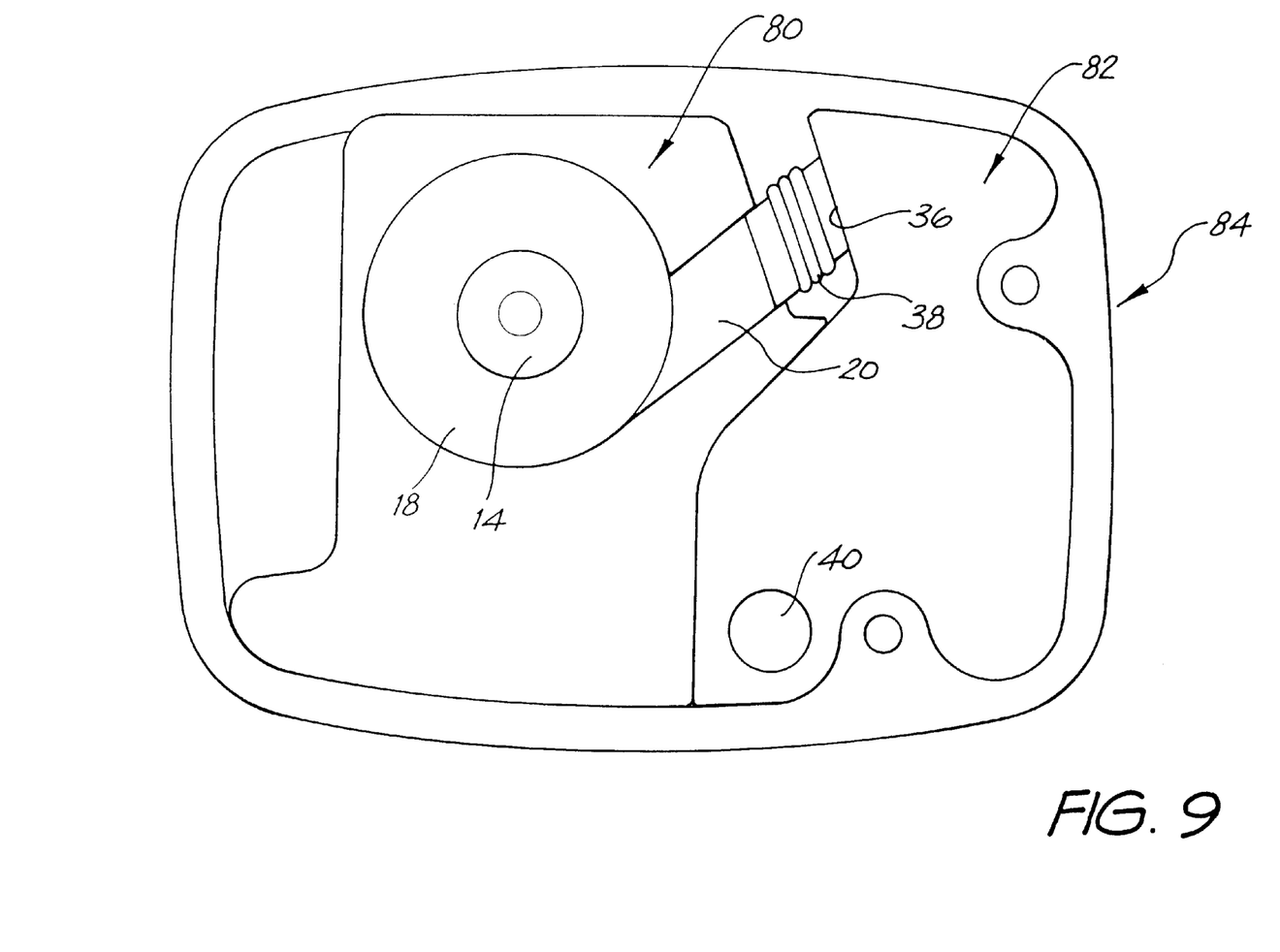
FIG. 9 is a plan view of the body shown in FIG. 7 adjacent a muffler and within a breathable gas supply apparatus housing.

FIGS. 7 to 9 show a third embodiment of a unitary mounting body 80 according to the invention in which like reference numerals for the first and second embodiments denote like features. FIG. 9 shows the mounting body 80 upon assembly adjacent a complementary shaped muffler 82 within a breathable gas supply apparatus housing 84.

Figure 10:
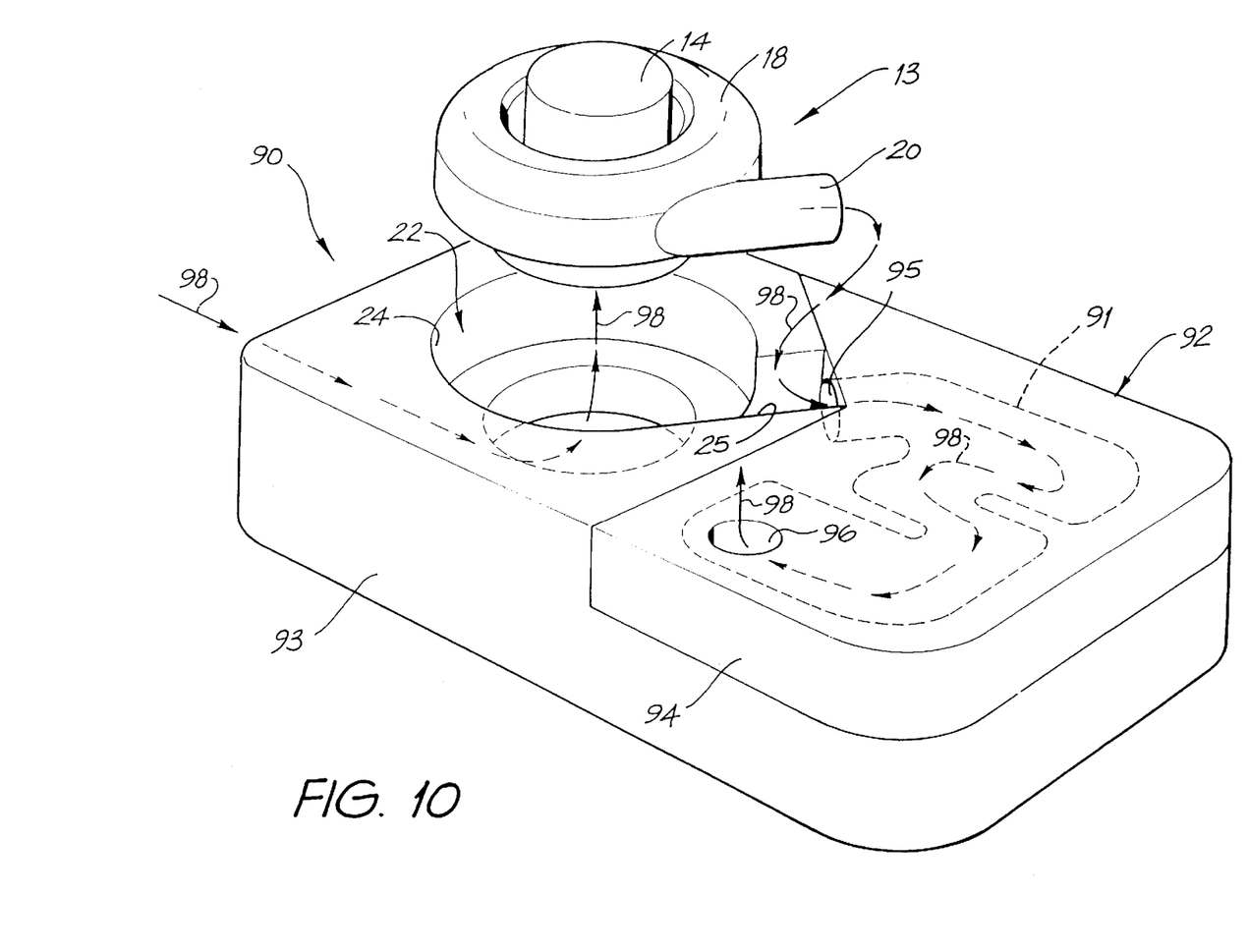
FIG. 10 is a perspective view of the fourth embodiment of a mounting body.

FIG. 10 shows a fourth embodiment of a mounting body 90 that includes an integral outlet muffler 92 shown in phantom. The body 90 includes a main block 93 having a recess and a complimentary shaped insert 94. One or other or both of the block 93 and the insert 94 include a recess which defies the tortuous cavity or chamber 91 of the outlet muffler 92 between muffler inlet 95 and muffler outlet 96. The insert 94 is adhered/bonded to the block 93. The body exterior is then sealed with a coating, for example FLEX-ANE LIQUID 60 from DEVCON, so pressurised air will not leak through the body 90 or the insert 94 in preference to flowing through the muffler outlet 96. The air flow path through the block 90 and insert 94 is generally indicated by arrows 98.

Figure 11:
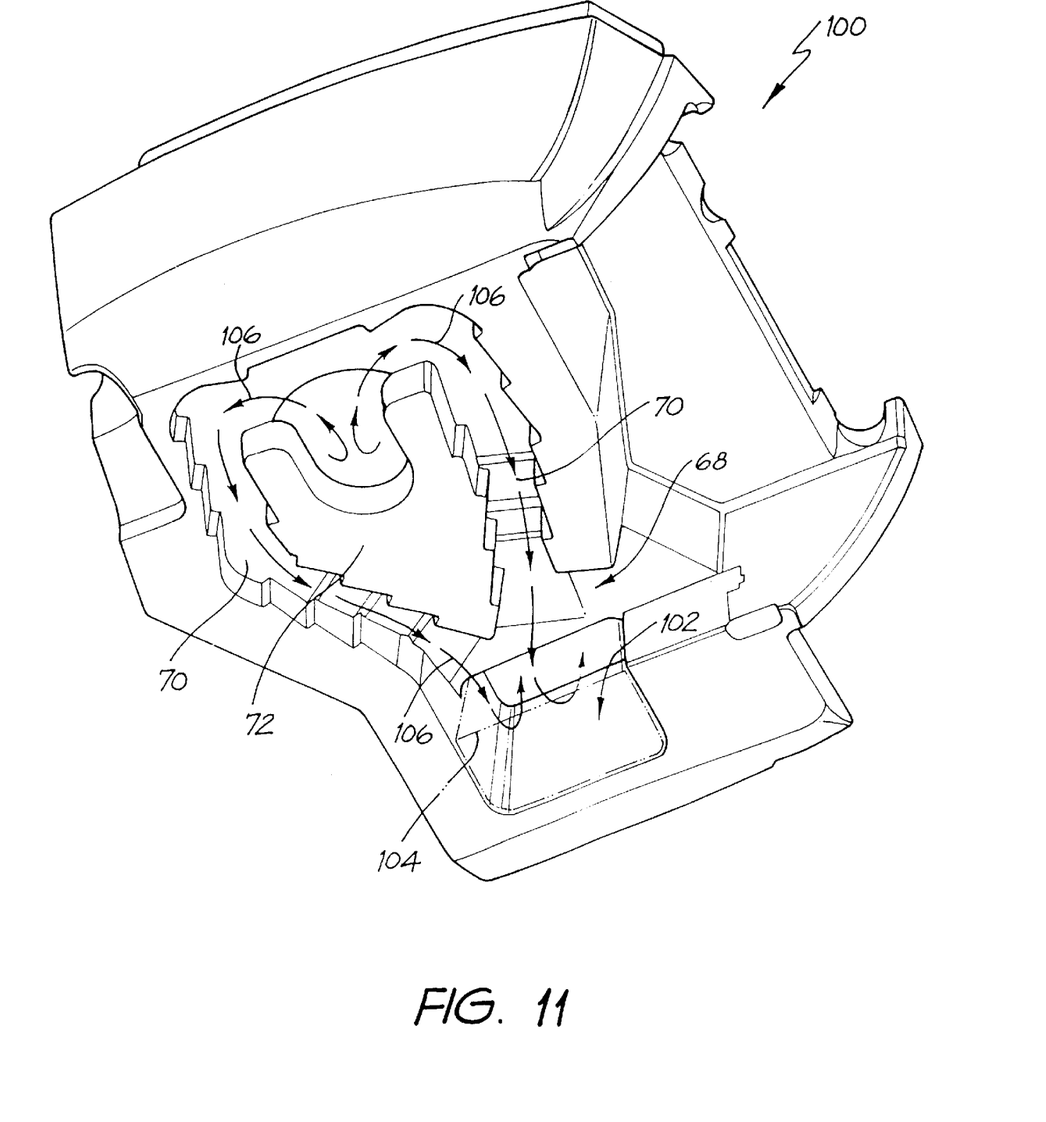
FIG. 11 is an underside perspective view of a fifth embodiment of a mounting body.

FIG. 11 shows the underside a fifth embodiment of a mounting body 100 which includes a recess 102 to locate a block 104 indicated in phantom (not shown) of a relatively more open cell sound absorptive foam than the body 100.

Sound waves (noise) travelling opposite to the gas flow direction from the flow generator assembly along the channels 70, as indicated by arrows 106, are reduced as they reflect from, or are partially absorbed by, the more sound absorptive block 104. Noise travel is also reduced by the non-smooth profile of the channels 70. The surfaces of the channels can also be corrugated or otherwise have a textured, irregular or rough surface to attenuate noise by promoting internal reflections and the like.

In a sixth embodiment of the invention (not shown) the mounting body has its external sides and underside coated with a hard plastics skin which serves as the apparatus housing. This embodiment of the invention combines the mounting device and apparatus housing into a single component and further simplifies manufacture and assembly. In an alternative form of the sixth embodiment (not shown), the body is moulded with an internal density gradient ranging from more dense and relatively rigid at the exterior walls to less dense and relatively resilient or compliant at the interior walls.

In a seventh embodiment (not shown) the body is produced from SORBATHANE (Trade Mark) and comprises a plastics skin around gel-filled cavities.

In an eighth embodiment (not shown), the mounting body includes a plurality of depressions, perforations, honeycombs, sub-ducts or sub-channels opening from the channel means and/or inlet duct and extending away therefrom into said mounting body. The depression, perforations, honeycombs, sub-ducts and/or sub channels improve the noise absorbing properties of the mounting body.

In a ninth embodiment (not shown), the mounting body is releasably mounted to the apparatus housing of the breathable gas providing apparatus so as to permit removal and replacement of the mounting body. This permits simple and quick replacement, cleaning and/or sterilisation of the channels means and/or the inlet duct that constitute the gas flow path through the mounting body.

In a tenth embodiment (not shown), the mounting body is shaped for supporting and locating other components of the breathable gas providing apparatus. As an example, the mounting body can include a recess to receive and locate an electrical control panel. Alternatively, the mounting body can include one or more protuberances or other support structures to support said control panel.

It is thought that the embodiments of the mounting bodies described above reduce radiated and transmitted noise in several different ways.

Firstly, the acoustically absorptive properties of the compliant body attenuate noise radiated from the flow generator assembly thereby reducing the level of noise reaching the apparatus housing.

Secondly, the body acts as a dampener and isolator to reduce the transfer of vibration from the flow generator assembly to the housing and lessoning apparatus vibration and the like.

Thirdly, noise produced by air being drawn into the flow generator inlet is also reduced as three of the four walls of the inlet duct are formed from the acoustically absorptive foam. A similar effect is achieved in respect of noise propagated from the flow generator assembly towards the patient mark conduit when the outlet muffler housing is also produced from a similar compliant material.

Further, noise from the flow generator assembly propagating through the inlet path opposite the gas flow direction is reduced as it must travel along the corrugated, tortuous path of the inlet channels through the compliant material in order to exit the apparatus housing at the air inlet.

A comparative test of a flow generator assembly with and without the mounting body of FIGS. 1 and 2 has been performed, and gives the following results for measured sound pressure level ($L_{eq}$) at 0.5 m:

| Condition | $L_{eq}$ (dBA) |
| --- | --- |
| Without Mounting Body | 66 |
| With Mounting Body | 51 |

The above described embodiments of the invention possess numerous advantages over the mounting devices and methods of the prior art.

Firstly, as discussed above, the breathable gas apparatus utilizing the mounting bodies previously described can be configured to be quieter than those of the prior art.

Secondly, assembly of the gas supply apparatus utilizing the mounting bodies of the present invention is simpler and thereby less expensive than those of the prior art as assembly is basically accomplished by pressing the flow generator assembly into the snug recess of the body and then placing the body in the flow generator housing for retention by the cover plate. This is in contrast to the prior art assembly procedure which involved bolting or screwing the flow generator assembly to the housing and/or other components and then attaching, numerous blocks of acoustically absorptive foam to the internal walls of the flow generator housing.

Assembly is especially simple with the fourth, fifth and sixth embodiments.

The cost of the compliant components are also less than that of the plastics and metal components thereby reducing overall apparatus cost.

Further, embodiments of the invention allow the apparatus to be rapidly and cheaply repaired or cleaned by disposing of those components that form part of the gas supply path, including, for example, the entire mounting body. Inexpensive replacement of the air path components obviates the need to sterilise the apparatus which is especially advantageous for breathable gas supply apparatus used, for example, in hospitals to treat a number of different patients. Prior art apparatus must be sterilized each time a different patient is treated. This advantage is enhanced in the fourth embodiment in which nearly all the components in the flow path are formed from compliant material.

Although the invention has been described with reference to specific examples, it will be appreciated by those skilled in the art, that the invention may be embodied in many other forms.

We claim:

1. A mounting body for mounting a flow generator assembly within an external housing, the body being formed from a compliant material and adapted to be fixed with respect to such an external housing and including a recess of substantially complementary shape to such a flow generator assembly to receive and locate same.

2. A mounting body as claimed in claim 1, wherein the mounting body includes one or more external surfaces adapted to be complementary to, and engage with, adjacent internal surfaces of such an external housing to locate the body with respect to such an external housing.

3. A mounting body as claimed in claim 1, wherein the mounting body is produced from a single piece of compliant material.

4. A mounting body as claimed in claim 1, wherein the body is formed from a plurality of compliant components fitted, adhered or otherwise bonded to one another.

5. A mounting body as claimed in claim 1, wherein the body includes a recess adapted to snugly receive such a flow generator assembly therein.

6. A mounting body as claimed in claim 5, wherein said recess is adapted to substantially envelope such a flow generator assembly.

7. A mounting body as claimed in claim 5, further including a foam insert adapted to cover any exposed surfaces of such a flow generator assembly.

8. A mounting body as claimed in claim 5, wherein the recess includes an orifice for allowing gas to communicate with an inlet of such a flow generator.

9. A mounting body as claimed in claim 8, wherein the mounting body includes as least one wall disposed, after assembly with such a flow generator assembly and external housing, adjacent an internal wall of such an external housing, said body wall including channel means which co-operate with such a housing internal wall to provide an inlet duct from atmosphere to the orifice.

10. A mounting body as claimed in claim 9, wherein a layer of compliant material is disposed between the housing wall and the body, the layer co-operating with the channel means to form the inlet duct.

11. A mounting body as claimed in claim 10, wherein the flow generator recess is on the opposite side of the mounting body to the inlet duct with the orifice providing fluid communication therebetween.

12. A mounting body as claimed in claim 9, wherein surfaces of the channel means are corrugated, textured, irregular or rough.

13. A mounting body as claimed in claim 8, wherein an inlet duct is formed internal of the mounting body for allowing communication from atmosphere to the orifice.

14. A mounting body as claimed in claim 9, wherein the inlet duct is a tortuous path to reduce noise propagating from the flow generator assembly to the apparatus air inlet.

15. A mounting body as claimed in claim 10, wherein the mounting body includes a plurality of depressions, perforations, honeycombs, sub-ducts or sub-channels opening from the channel means and/or the inlet duct and extending away therefrom into said mounting body.

16. A mounting body as claimed in claim 1, wherein the body is shaped to isolate such a flow generator from any contact with the housing.

17. A mounting body as claimed in claim 1, wherein the mounting body is formed from a substantially open cell polyurethane foam.

18. A mounting body as claimed in claim 17, wherein the polyurethane foam is 1SF-1350 type manufactured by URETEC.

19. A mounting body as claimed in claim 1, wherein the recess is substantially cylindrical.

20. A mounting body as claimed in claim 1, wherein the mounting body includes an integral outlet muffler.

21. A mounting body as claimed in claim 1, wherein the exterior of the mounting body is sealed.

22. A mounting body as claimed in claim 21, wherein the exterior is sealed by coating with FLEXANE 60 manufactured by DEVCON.

23. A mounting body as claimed in claim 1, wherein the mounting body includes an insert in the gas flow path of the mounting body, the insert being a more open cell sound absorptive foam than the mounting body.

24. A mounting body as claimed in claim 1, wherein the mounting body includes a hard plastics exterior skin.

25. A mounting body as claimed in claim 1, wherein the mounting body defines exterior and interior walls, and is moulded with an internal density gradient ranging from more dense and relatively rigid at exterior walls to less dense and relatively resilient at interior walls.

26. A mounting body as claimed in claim 1, wherein the mounting body is produced from SORBATHANE and comprises a plastics skin around gel-filled cavities.

27. A mounting body as claimed in claim 1, wherein the mounting body is releasably mounted to such an external housing so as to permit removal and replacement of the mounting body.

28. An apparatus for providing breathable gas to a patient, the apparatus includes an external apparatus housing, a flow generator assembly, and a mounting body of compliant material fixed with respect to said housing including a recess of complementary shape to said flow generator assembly to receive and locate same.

29. An apparatus as claimed in claim 28, wherein the mounting body is shaped for supporting and locating other components of a breathable gas providing apparatus.

* * * * *